US008863364B2

(12) United States Patent
Gay et al.

(10) Patent No.: US 8,863,364 B2
(45) Date of Patent: Oct. 21, 2014

(54) PINCHING CLOSED A COLLAPSIBLE TUBE FOR BIOPHARMACEUTICAL USE

(75) Inventors: Isabelle Valerie Christine Gay, Peypin (FR); Michael Bates, Gloucestershire (GB); Ray Bassett, Gloucestershire (GB); Chris Biddel, Gloucestershire (GB)

(73) Assignee: Sartorius Stedim FMT SAS, Aubagne (FR)

( * ) Notice: Subject to any disclaimer, the term of this patent is extended or adjusted under 35 U.S.C. 154(b) by 630 days.

(21) Appl. No.: 13/133,834

(22) PCT Filed: Nov. 24, 2009

(86) PCT No.: PCT/FR2009/052284
§ 371 (c)(1),
(2), (4) Date: Aug. 11, 2011

(87) PCT Pub. No.: WO2010/066978
PCT Pub. Date: Jun. 17, 2010

(65) Prior Publication Data
US 2011/0284776 A1 Nov. 24, 2011

(30) Foreign Application Priority Data
Dec. 10, 2008 (FR) .................................. 08 06952

(51) Int. Cl.
B23P 11/00 (2006.01)
B21D 39/00 (2006.01)
B23P 19/00 (2006.01)
F16K 7/04 (2006.01)
A61M 39/28 (2006.01)
A61M 39/14 (2006.01)

(52) U.S. Cl.
CPC ............. *A61M 39/28* (2013.01); *A61M 39/146* (2013.01)
USPC ................ 29/243.5; 29/524.1; 29/798; 251/7

(58) Field of Classification Search
USPC ........................................................ 29/243.5
See application file for complete search history.

(56) References Cited

U.S. PATENT DOCUMENTS 3,042,067 A * 7/1962 Hidding ................... 137/315.07
3,588,034 A 6/1971 Powell
(Continued)

FOREIGN PATENT DOCUMENTS

EP 0 623 450 A1 11/1994
EP 0 778 123 A2 6/1997
(Continued)

OTHER PUBLICATIONS

International Search Report, dated Mar. 25, 2010, from corresponding PCT application.

*Primary Examiner* — Lee D Wilson
*Assistant Examiner* — Alvin Grant
(74) *Attorney, Agent, or Firm* — Young & Thompson

(57) ABSTRACT

The pinching device includes two cross-sections, each having a hollow part with a male indentation and a female indentation, and locking elements, whereby the surfaces of the indentations form a positive pinching passage of the tube; the male indentation has a U shape with a core and two wings; the female indentation has a U shape with a core and two wings; and the pinching passage has a U shape with a core and two wings; the two opposite wings will draw together toward their ends that are opposite to the cores of the indentations, and each of the two wings of the pinching passage has an opening whose width will diminish towards its end that is opposite to the core of the pinching passage; the width of the opening of the pinching passage is at most slightly smaller than twice the thickness of the wall of the flexible tube to be pinched, and, designed to constitute a pinching closing device, it is disposable, performing a function of closing the tube on itself in the pinching region, preventing any passage of fluid into the tube.

19 Claims, 6 Drawing Sheets

(56) References Cited

U.S. PATENT DOCUMENTS

Figure 1:
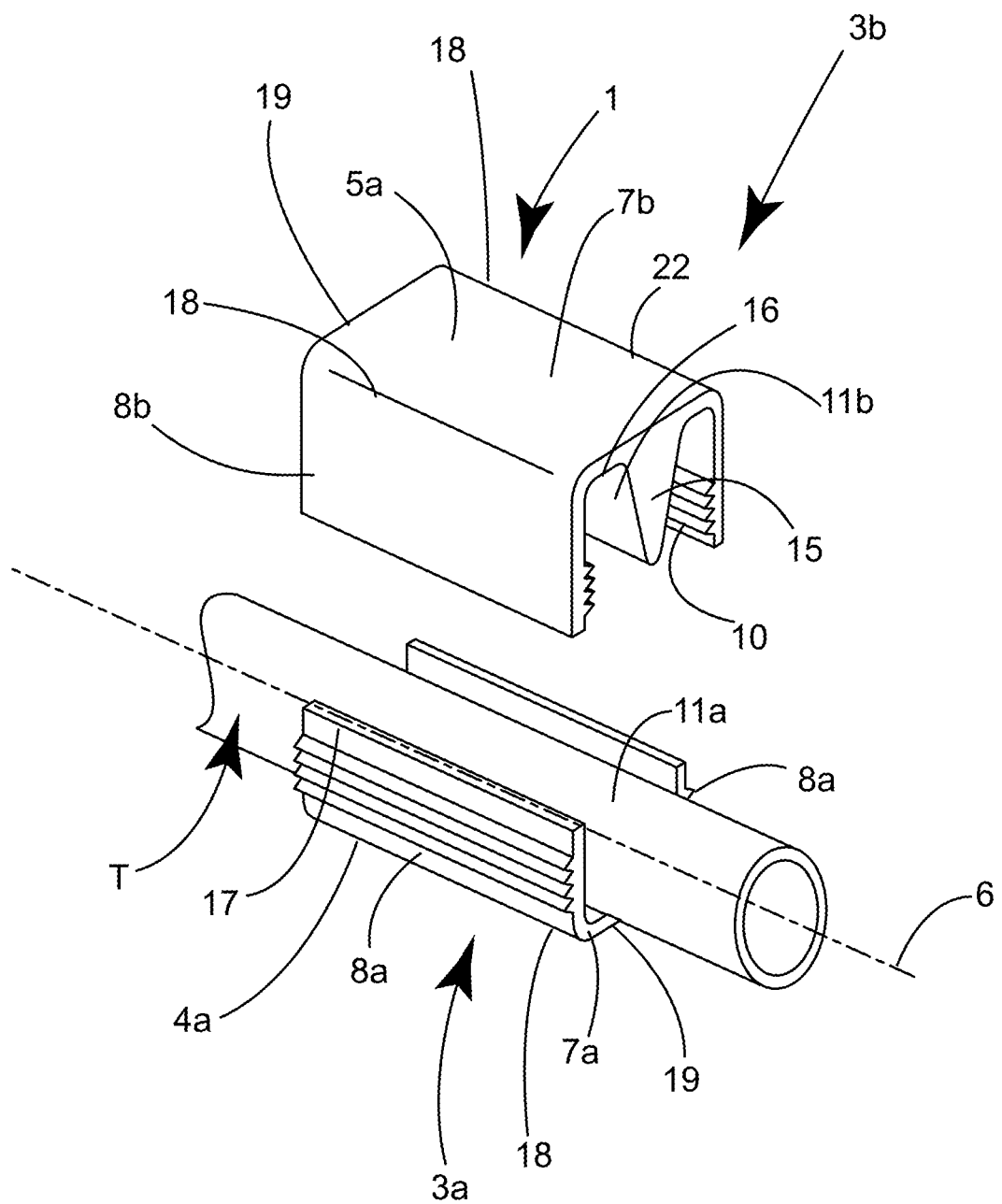

| | | |
|---|---|---|
| 3,942,228 A | 3/1976 | Buckman et al. |
| 4,337,791 A * | 7/1982 | Tech et al. .................... 137/556 |
| 4,429,852 A | 2/1984 | Tersteegen et al. |
| 4,688,753 A | 8/1987 | Tseng et al. |
| 5,238,218 A | 8/1993 | Mackal |
| 5,305,517 A * | 4/1994 | Schleicher .................... 29/798 |
| 5,925,023 A * | 7/1999 | Hiejima ........................ 604/246 |
| 6,089,527 A | 7/2000 | Utterberg |
| 6,554,589 B2 * | 4/2003 | Grapes .................... 417/477.12 |
| 6,742,760 B2 | 6/2004 | Blickhan et al. |
| 7,410,155 B2 | 8/2008 | Spain, III |
| 8,141,227 B2 * | 3/2012 | Nishimura et al. .......... 29/524.1 |
| 8,332,999 B2 * | 12/2012 | Karling et al. ............... 29/243.5 |

FOREIGN PATENT DOCUMENTS

| | | |
|---|---|---|
| FR | 2 323 939 A1 | 4/1977 |
| FR | 2 492 261 A1 | 4/1982 |
| FR | 2 688 285 A1 | 9/1993 |

\* cited by examiner

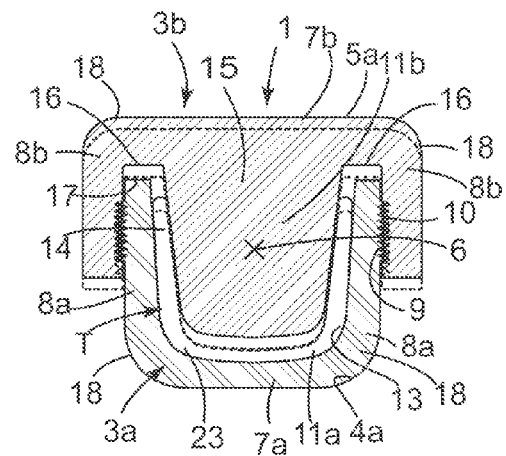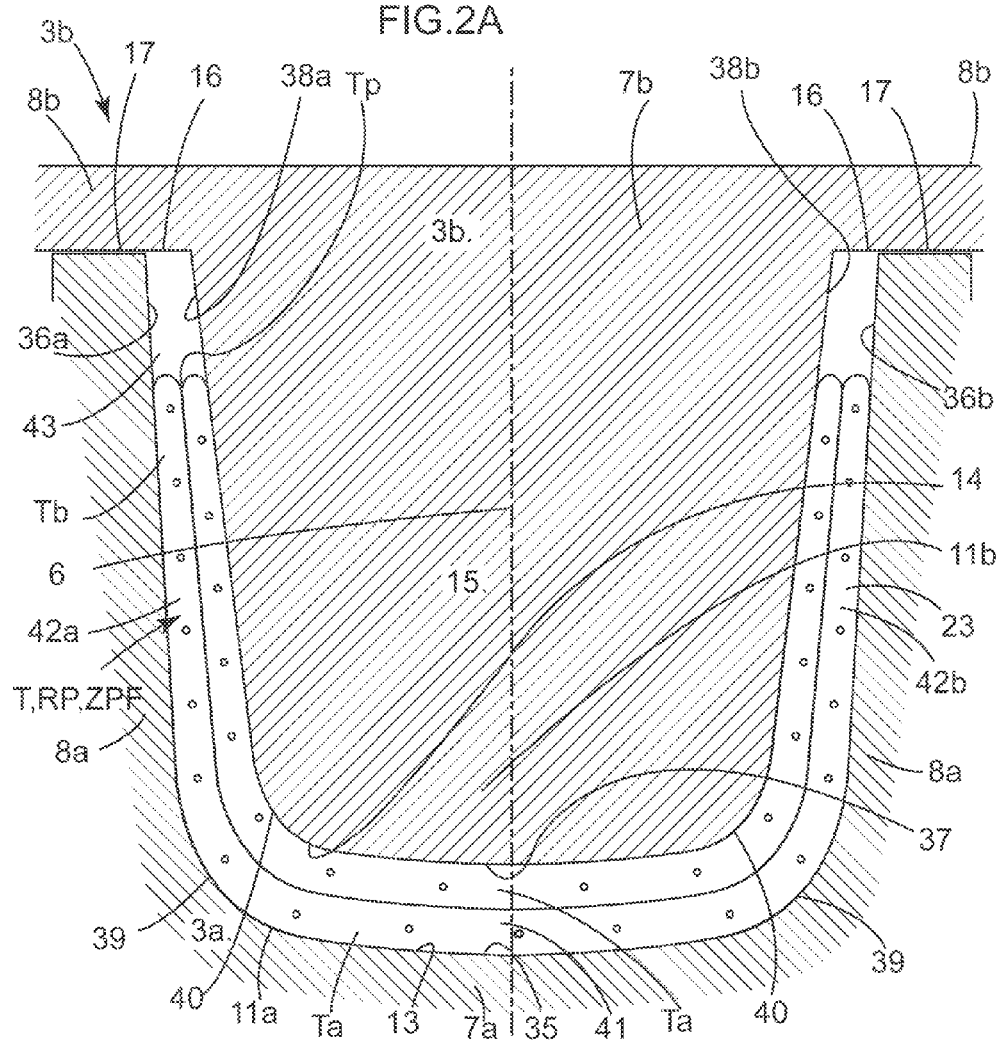

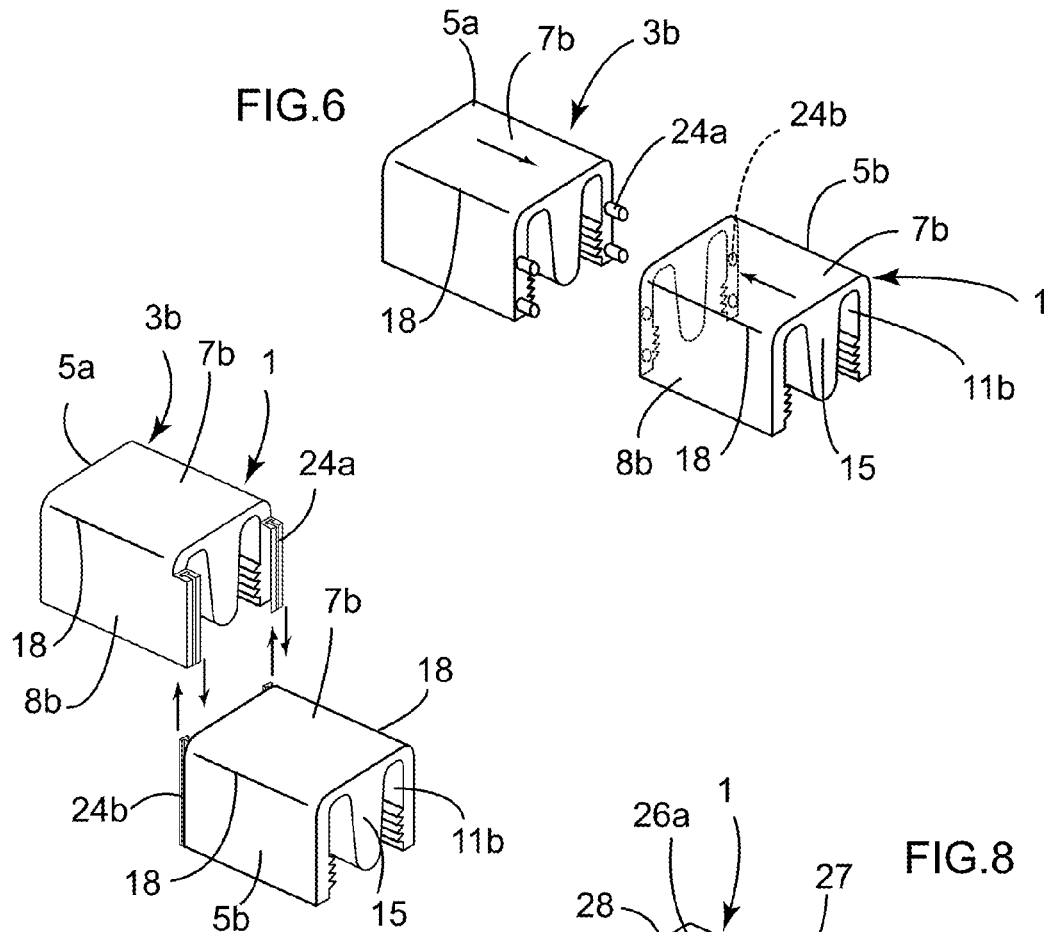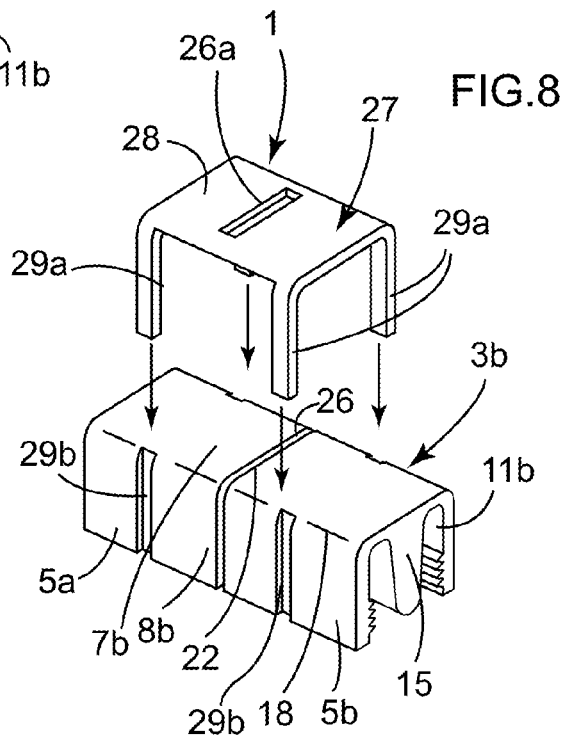

PINCHING CLOSED A COLLAPSIBLE TUBE FOR BIOPHARMACEUTICAL USE

Background of the invention

The invention has as its object a device 1 for pinching closing of a flexible tube in a pinching region and, according to one embodiment, a pinching closing unit for cutting into sections such a tube.

Description of the Related Art

In a typical embodiment in the biopharmaceutical field, such a tube has an outside diameter of between, for example, 8 millimeters and 30 millimeters, whereby the thickness depends on material, diameter, and applications.

Most often, such a tube either is part of a device that comprises one or more pockets or functional means (filtration, mixing, . . . ) or it is mounted on, and functionally combined with, a processing apparatus or device (sampling, circulation, . . . ).

In certain cases, the process that involves the fluid that is channeled by the tube at one time or another requires that the tube be closed in a given region so as to prevent the passage of fluid. If necessary, the process requires that the tube be not only closed but also cut into sections transversally in—or at least in the vicinity of—the closing region.

Clamps for closing flexible tubes used in the biopharmaceutical field, known under the name of Halkey clamps or Roberts clamps or else Halkey-Roberts clamps, are known. Such a clamp comprises a deformable plastic part of a general annular shape, having two free end parts for reciprocal hooking opposite, a passage for the tube opposite them, two projections directed toward the median part of the clamp, each between a hooking part and the passage. Once the clamp is placed on a tube and then closed by cooperation of the two hooking parts, the two projections pinch the tube that is placed between them in a point or almost-point pinching zone. It is possible to refer to, for example, the documents U.S. Pat. Nos. 3,942,228, 6,089,527 and 6,742,760. Such clamps are suitable for a temporary and reversible use, but they are not suitable for a permanent and irreversible use.

The document U.S. Pat. No. 4,688,753 describes a device for pinching a flexible tube in a pinching region, comprising two parts with male and female indentations, able to be either in the open state where they are separated from one another or in the closed state where they are drawn together and closed on one another by reciprocal-locking means and where the faces of the indentations form a passage for pinching the tube. Although the document U.S. Pat. No. 4,688,753 does not describe the locking means, it provides that the latter are reversible, with the pinching device being designed to be able to be closed and open multiple times. Such a device is not disposable. The document U.S. Pat. No. 4,688,753 describes male and female indentations that, for their active pinching part, have specific flattened shapes with divergent lateral edges whose separation is then greater than twice the thickness of the wall of the flexible tube to be pinched, in such a way that the tube is not completely closed on itself with the risk of fluid passing into the pinching region.

The document FR 2 688 285 describes a device for blocking a pipe for draining a urostomy bag that comprises a cylindrical sleeve, a deformable support part on the flexible pipe to reduce its internal cross-section for passage of fluid and a ring mounted to rotate on the sleeve. The rotation of the ring around the sleeve causes the ends of the deformable support part that has an elongated shape to draw together, and consequently the support of the central part is drawn together on the flexible pipe until the latter is flattened. The purpose of this device is to be able to control the flow of fluid easily in the pipe during the opening.

The document U.S. Pat. No. 7,410,155 describes a clamp for pinching a deformable tube that is intended for biopharmaceutical applications and that comprises a first cross-section and a second cross-section that are articulated with one another, with each cross-section itself having two articulated parts between them. The first and the second cross-sections are arranged in such a way as to be able to be moved to pivot in a way relative to one another between an open position and a closed position. The four parts comprise a recessed indentation with a flat bottom that comes over the tube on either side for pinching it. The clamp also comprises reciprocal-locking means of the two parts of each pair of parts of the two cross-sections to keep them at least temporarily in place in the closed position. Such a device is intended to be cut into sections to be able to cut the tube into sections. A clamp of this structure has numerous drawbacks. The use of hinges does not make possible a uniform compression of the tube. The pinching is achieved by a flat compression with the inherent risk of leakage. The clamp is not suitable for tubes of different geometries (diameter and/or thickness).

Summary of the Invention

The purpose of the invention is to propose a pinching closing device that is disposable and performs a permanent closing function of the tube on itself in the pinching region, preventing any passage of fluid into the tube, which the devices according to the documents of the prior art do not allow. Actually, the requirement for a closing that prevents any passage of fluid into the tube is all the more important as the closing is permanent; in any case, there is no call for it to be reversible, whereby this requirement is less crucial in the case of a temporary and reversible closing.

The object of the invention is to propose such a device that is inexpensive, easy to manufacture, and simple and reliable to use all at the same time. Actually, such a device should be able to be installed readily but effectively over the course of the process involving the fluid that is channeled by the tube.

For this purpose, according to a first aspect, the invention proposes a pinching closing device of a flexible tube in a pinching region, comprising two cross-sections, each having a hollow part with male and female indentations, respectively, able to be either in the open state where they are separated from one another or in the closed state where they are drawn together and closed on one another by reciprocal-locking means and where the surfaces of the indentations form a positive pinching passage of the tube.

This device is such that:

In the transverse straight cross-section, the male indentation has a U shape with a core and two wings; in the transverse straight cross-section, the female indentation has a U shape with a core and two wings; and in the transverse straight cross-section, the pinching passage has a U shape with a core and two wings, The two wings opposite each pair of wings facing the male indentation and the female indentation will draw together toward their ends that are opposite to the cores of the indentations, at least in the zone of these ends, and each of the two wings of the pinching passage has, between the surfaces of the two indentations, an opening whose width will diminish towards its end that is opposite to the core of the pinching passage, The width of the opening of the pinching passage is at most slightly smaller than twice the thickness of the wall of the flexible tube to be pinched.

The pinching closing device is disposable and performs a function of closing the tube on itself in the pinching region preventing any passage of fluid into the tube.

According to another characteristic, the locking means are irreversible, whereby the two cross-sections, once brought into the closed state, are held in place in this state by locking means without being able to be dissociated, whereby these locking means comprise contoured hooking teeth (or the like), oriented in two opposite directions.

According to a first embodiment, the two cross-sections are two separate parts and are brought into the closed state by a relative transverse sliding movement relative to the longitudinal axis of the device.

According to one option, one of the two cross-sections is a male cross-section and the other is a female cross-section, with the male cross-section comprising and being limited on the outside by a first core and two first lips, and with the female cross-section comprising and being limited on the outside by a second core and two second lips.

According to one option, the separation between the two opposite outside surfaces of the two first lips corresponds to the separation between the two inside surfaces opposite the two second lips, in such a way as to make possible, in the closed state of the device, interlocking with adjustment of the two cross-sections, whereby the pair of outside surfaces is then in contact and supported on the pair of inside surfaces.

According to one option, the reciprocal-locking means are two units that comprise a series of teeth respectively made on the two outside surfaces of the first lips and the two inside surfaces of the second lips in their interlocking zone.

According to one option, the male cross-section defines a female indentation, and the female cross-section defines a male indentation.

According to a second embodiment, the two cross-sections are two parts that are combined structurally with one another to pivot around an axis that, relative to the longitudinal axis of the device, is offset on one longitudinal side of the device, with the two cross-sections being brought into the closed state by a relative pivoting movement around the pivoting axis.

According to one option, the reciprocal-locking means comprise teeth that are located on the side that is opposite to the pivoting axis of the two cross-sections.

According to one characteristic, the cross-sections are contoured and extend along the longitudinal axis of the device, whereby the positive pinching closing zone extends over a certain axial length, not being a point or quasi-point pinching zone.

According to one option, the reciprocal-locking means comprise a female part that is connected to one of the parts of the cross-section and that is equipped with teeth, and a male part that is connected to the other part and that is equipped with teeth.

According to one characteristic, the two cross-sections have the same axial length.

According to a first variant, the two indentations have the same shape, the same arrangement, and the same dimensions, constant and uniform, from one free end to the next.

According to a second variant, one and/or the other of the two indentations is slightly inclined along the longitudinal axis of the device, toward the free border of the edge of the lip and toward the proximal end, for exerting a more significant pinching of the tube toward the proximal end and for expelling the fluid that is found in the tube toward the distal end.

According to one option, the pinching passage has an adjustable opening, with the relative movement for bringing one cross-section opposite the other and the device in the closed state being more or less large, so that the pinching passage is respectively more or less small. According to one possible embodiment, the device comprises a series of stepped hooking teeth, making possible different relative locking positions of the cross-sections so that the pinching passage is more or less small.

According to one conceivable embodiment, each cross-section comprises two hollow parts that are placed in the extension of one another by combination means, with at least one pair of the parts having indentations.

According to the implementations, the two hollow parts of each cross-section are analogous, with the device ensuring a closing function of the tube on itself in two positive pinching closing zones, or, in contrast, the two hollow parts are different, with the device ensuring a closing function of the tube on itself in a single positive pinching closing zone and being only held in place in the other zone.

According to the implementations, the locking means are irreversible for the two pairs of hollow parts or irreversible for one of the pairs of hollow parts and reversible for the other. More specially, the locking means are reversible for a pair of hollow parts ensuring only a simple holding in place of the tube T.

According to the implementations, the combination means comprise at least one projection made on one of the parts, able to work in a removable way with at least one blind hole or hollow or groove that is complementary, made on the other part of the same cross-section, or comprise at least one removable connecting part in clip form, able to combine the two parts in a removable way and in an indirect way, or comprise a removable connecting part that is in the shape of a cradle.

According to the embodiment in question, the hollow parts are placed in the extension of one another by making between them a median passage that empties onto the outside surface of the device by an access, whereby the positive pinching closing passage comprises at least one segment to which a space—into which the passage empties and where the tube is held in place, on the one hand, and flattened to a certain degree, on the other hand—is axially adjacent.

In this case, the functions of the access, on the one hand, and the median passage and the space, on the other hand, are respectively to allow, on the one hand, the introduction, and, on the other hand, the passage of an element for cutting the tube in its zone located in said space.

According to a second aspect, the invention proposes a pinching closing unit for cutting into sections that comprises a device as it was just described and a cutting element, functionally combined, whereby the cutting element is able to be introduced into the device by the access provided for this purpose and to pass into the median passage and the space so as to cut the tube in its zone located in the space, without the cutting element being cut into sections, penetrating into or interfering frontally with the device.

BRIEF DESCRIPTION Of The DRAWING FIGURES

Figure 3:
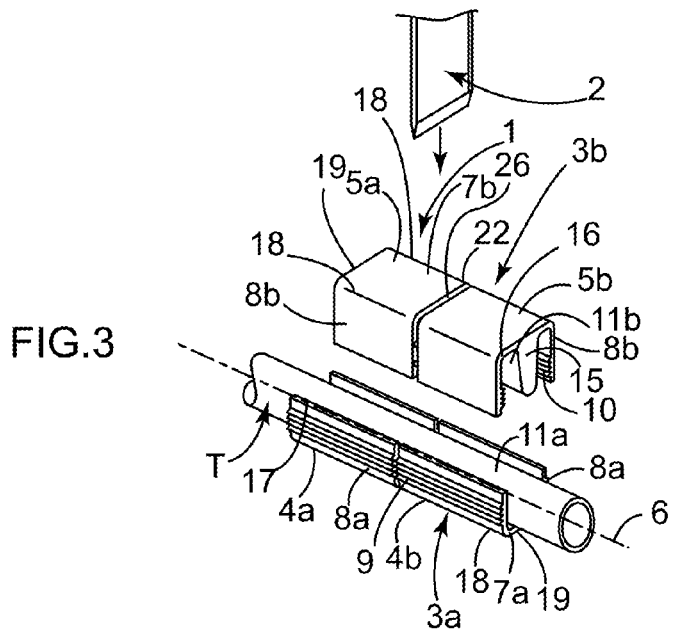
Figure 4:
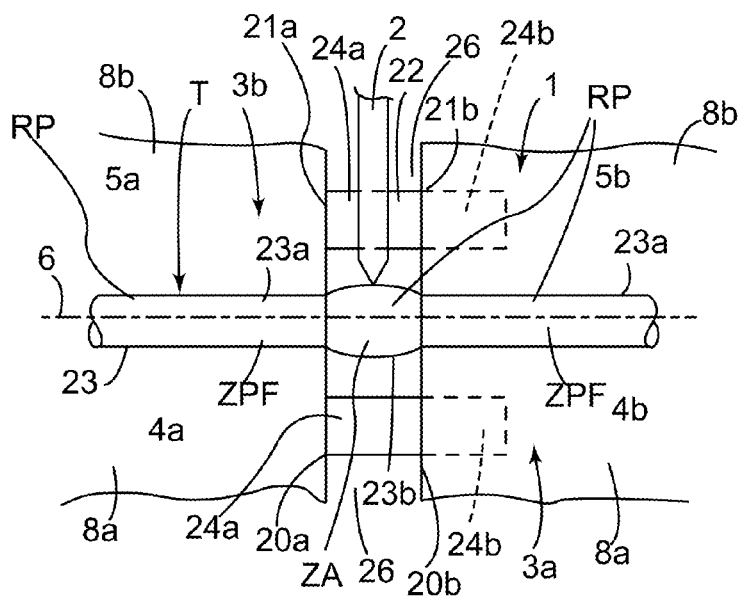
Figure 5:
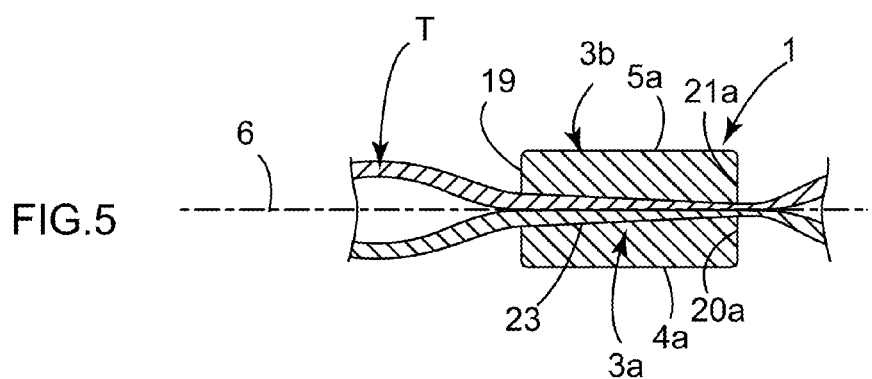
Figure 9:
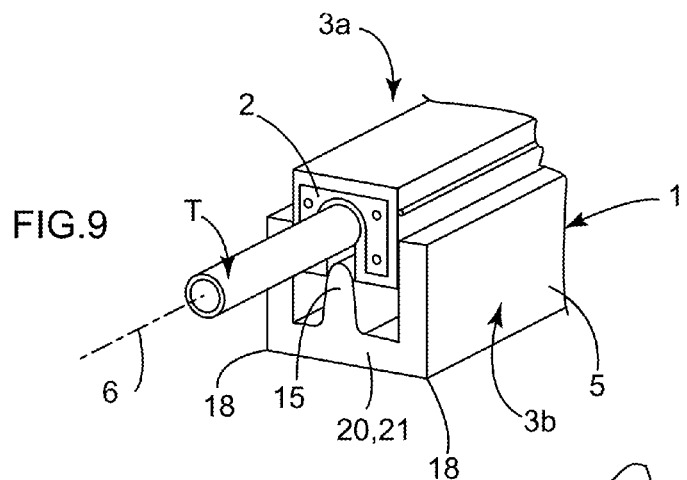
Figure 10:
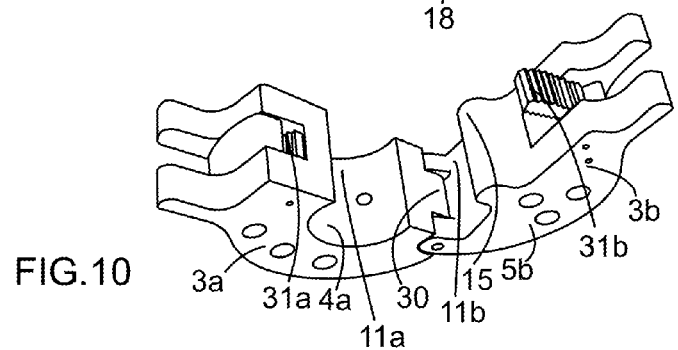
Figure 11:
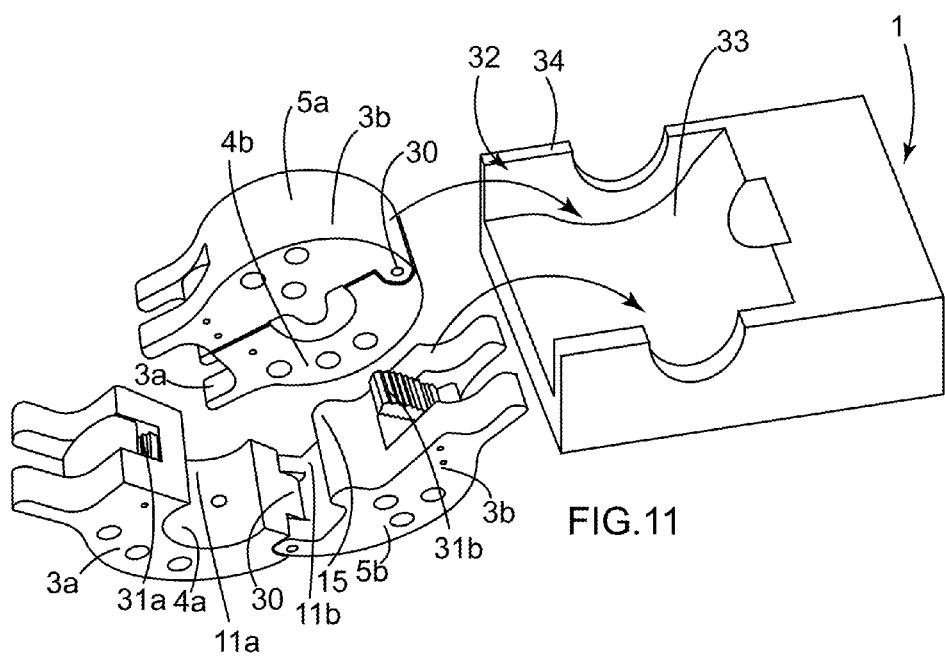
Figure 12:
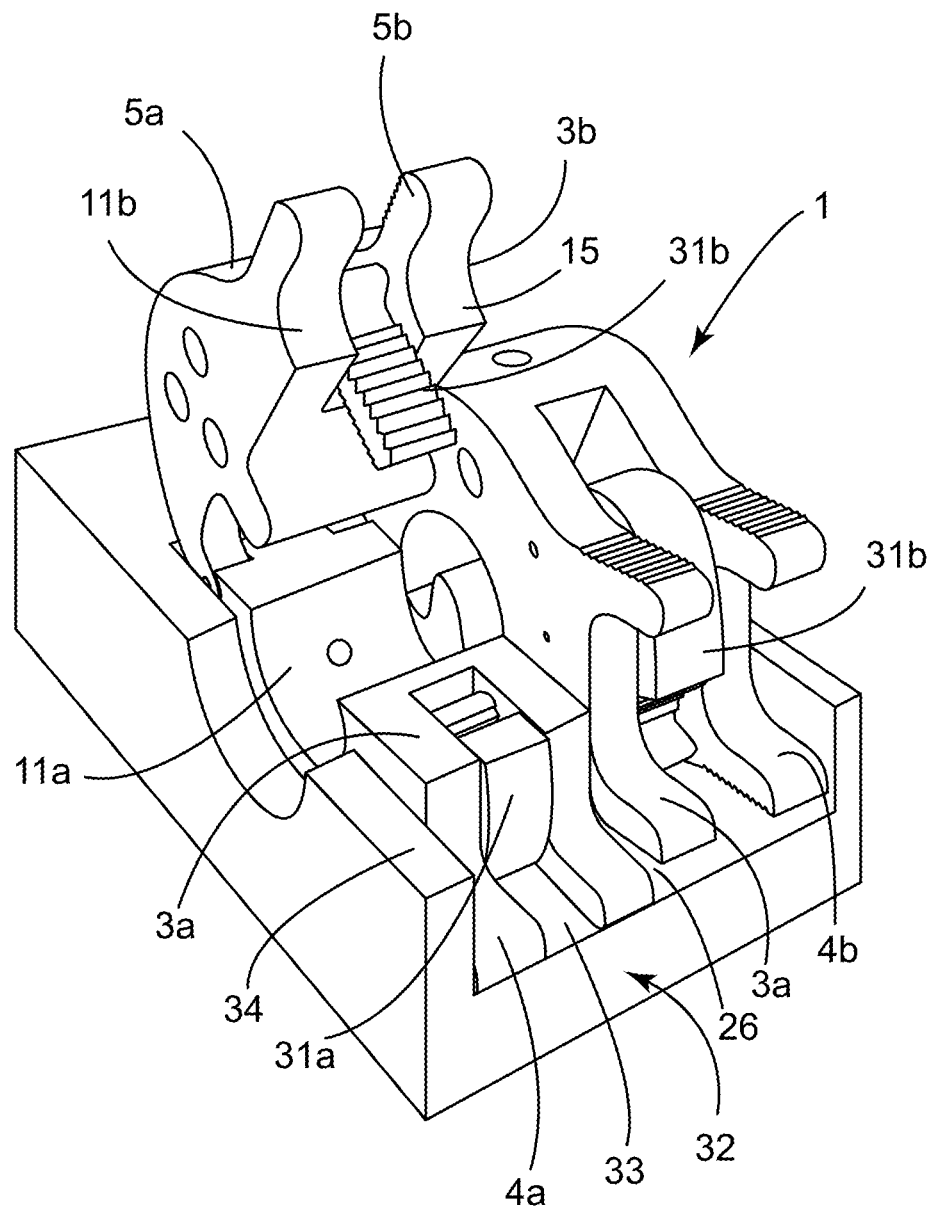

Several embodiments of the invention are now described using drawings in which:

FIG. 1 is a perspective view of a possible embodiment of a pinching closing device in the open state, with a portion of the tube in position, in which the two cross-sections of the device are two separate parts and are brought into the closed state by a relative transverse sliding movement relative to the longitudinal axis of the device, FIG. 2 is a transverse cutaway view of the pinching closing device in the closed state, with a portion of the tube in position, FIG. 2A is a partial view on a larger scale of FIG. 2, FIG. 3 is a perspective view of a possible embodiment of a pinching closing unit for cutting into sections that comprises a pinching closing device of the type of the one of FIG. 1, in a double embodiment, in the open state, with a portion of the tube in position, a cutting element being shown diagrammatically, FIG. 4 is a partial, axial cutaway view on a larger scale of the pinching closing unit for cutting into sections and a portion of the tube in position, just before the beginning of cutting the tube into sections, FIG. 5 is a longitudinal cutaway view of a possible embodiment of a pinching closing device in the closed state, with a portion of the tube in position, FIGS. 6, 7 and 8 are three perspective views of three possible embodiments of locking means of a pinching closing unit for cutting into sections that is shown partially, FIG. 9 is a perspective view of a possible embodiment of the cutting element combined with a pinching closing unit for cutting into sections that is shown partially, FIG. 10 is a perspective view of a possible embodiment of a pinching closing device in the open state, in which the two cross-sections of the device are two parts that are combined structurally with one another to pivot around an axis that, relative to the longitudinal axis of the device, is offset on a longitudinal side of the device, whereby the two cross-sections are brought into the closed state by a relative movement of pivoting around the pivoting axis, FIGS. 11 and 12 are two perspective views of a possible embodiment of a pinching closing unit for cutting into sections that comprises a pinching closing device of the type of the one of FIG. 10, in a double embodiment, respectively diassembled and assembled.

DETAILED DESCRIPTION Of The INVENTION

A pinching closing device 1 makes it possible to ensure a pinching closing of a tube T as defined above, in the desired region, the reason for which it is referred to as the pinching closing device 1. The pinching closing device 1, functionally combined with at least one cutting element 2, integrated or outside of it, forms a pinching closing unit for cutting into sections 1+2 that also makes it possible to ensure the transverse cutting into sections of the tube T.

Once the pinching closing device 1 has been implemented to ensure the positive pinching closing of the tube T and also, if necessary, its transverse cutting into sections, the purpose of the pinching closing device 1 is to remain attached to the tube T.

According to one characteristic, the pinching closing device 1 is disposable.

FIG. 1 illustrates a possible embodiment of a pinching closing device 1 that comprises two cross-sections 3, hollow, contoured, namely a first male cross-section 3a and a second female cross-section 3b.

The male cross-section 3a has a hollow and contoured part 4a, and the female cross-section 3b has a hollow and contoured part 5a.

FIG. 2 illustrates a pinching closing unit for cutting into sections 1+2 that comprises a pinching closing device 1 of the preceding type, but double, and the cutting element 2.

In this case, each cross-section 3a, 3b comprises two parts that are likewise hollow and contoured, namely, respectively, the two parts 4a and 4b for the male cross-section 3a and the two parts 5a and 5b for the female cross-section 3b.

In the case of a pinching closing unit for cutting into sections 1+2, the two cross-sections 3a and 3b are able, based on the operating phases, to be structurally and functionally combined with one another by a normally irreversible interlocking, for forming a rigid unit, with the two hollow parts being opposite (FIG. 4) (pinching phase, phase for cutting into sections), or to be dissociated (FIG. 3) (installation phase).

The two parts 4a and 4b or 5a and 5b of the same cross-section 3a or 3b are able, according to the operating phases, to be structurally and functionally combined with one another by being placed in the extension of one another (FIG. 3) (pinching phase, phase for cutting into sections), or to be dissociated (FIGS. 5, 6 and 7) (dissociation phase).

When the two cross-sections 3a and 3b are structurally and functionally combined with one another by interlocking, their respective opposite parts 4a and 5a, on the one hand, and 4b and 5b, on the other hand, are also structurally and functionally combined with one another by an interlocking that, under the normal conditions of use, is irreversible.

The cross-sections are generically referenced 3 and the parts 4 and 5.

The pinching closing device 1 therefore comprises the four separate parts 4a, 4b, 5a and 5b that are compact, contoured, rigid and typically made of plastic material such as a polymer that is selected for satisfying, if necessary, the other constraints that the pinching closing device 1 has to face, for example, withstanding treatment in an autoclave or by γ-radiation.

In one embodiment, the parts 4a and 4b of the cross-section 3a are, if not strictly identical, at least analogous with one another, likewise regarding the parts 5a and 5b of the cross-section 3b. In this case, the pinching closing device 1 ensures a function of closing the tube T on itself in two positive pinching closing zones.

However, in another embodiment, the two hollow parts 4a, 4b and 5a, 5b are not analogous, but different, in such a way that, for example, the pinching closing device 1 ensures a closing function of the tube T on itself only in a single positive pinching closing zone. In its other zone, the tube T is then simply held in place, which facilitates its transverse cutting into sections. If necessary, this holding in place can be removed, existing only as necessary for cutting into sections.

The pinching closing device 1 has a longitudinal axis 6 that is also the longitudinal axis of the tube T when the latter is placed in the pinching closing device 1. This is in relation to this axis 6 that describes as "axial" any direction or plane that extends parallel to the axis 6 and as "transverse" any direction or plane that extends orthogonally to the axis 6.

The two cross-sections 3a and 3b are contoured and extend along the axis 6.

In the embodiment shown, the two cross-sections 3a and 3b are one-piece and of the same axial length in such a way as to be able to be interlocked by being adjusted, opposite one another.

Each of the two cross-sections 3a and 3b, or each of its two parts 4a, 4b and 5a, 5b, has an outside contour that has a general U shape or a pseudo-U shape in a transverse, straight cross-section. This contour comprises and is limited by several segments, namely a core and, on either side of the latter, two lateral lips, whereby the core and the two lips furthermore extend axially.

The first male cross-section 3a comprises and is limited on the outside by a first core 7a and two first lips 8a. The second female cross-section 3b comprises and is limited on the outside by a second core 7b and two second lips 8b.

The separation between the two opposite outside surfaces 9 of the first two lips 8a corresponds to the separation between the two inside surfaces 10 opposite the second two lips 8b. This arrangement makes possible, in the closed state of the pinching closing device 1, the interlocking with adjustment of the two cross-sections 3a and 3b, or their constituent parts, whereby the pair of outside surfaces 9 is then in contact and supported on the pair of inside surfaces 10.

In the embodiment shown, the first male cross-section 3a defines a first female indentation 11a, and the second female cross-section 3b defines a second male indentation 11b.

According to another embodiment, the arrangement is reversed, with the first male cross-section 3a defining a first male indentation and the second female cross-section 3b defining a second female indentation (FIG. 9).

The first female indentation 11a is defined by a contoured surface 13, extending along the axis 6, having—in the transverse cross-section—a contour of the soffit of a U and extending parallel to the axis 6. The surface 13 consists of the inside surface 35 of the first core 7a, arranged in a median way, and two inside surfaces 36a and 36b of the first two lips 8a, arranged laterally on either side of the inside surface 35. Thus, the female indentation 11a comprises a core 35 and two wings 36a and 36b.

The second male indentation 11b is defined by a contoured surface 14, extending along the axis 6, having—in the transverse cross-section—a contour of the extrados of a U and extending parallel to the axis 6. The surface 14 consists of the outside surface 37 of the end part of a projection 15, arranged in a median way, and two outside surfaces 38a and 38b of the body of the projection 15, placed on either side of the outside surface 37. Thus, the male indentation 11b comprises a core 37 and two wings 38a and 38b.

The projection 15 is adjacent to the second core 7b and extends at an equal distance between the second two lips 8b by being directed in the same direction as they are.

The surface 14 is connected to the two inside surfaces 10 of the two lips 8b by two small, essentially coplanar surfaces 16. These two small surfaces 16 are able, if necessary—when the interlocking of the two cross-sections 3a and 3b is the largest—to be in contact and supported on the two free edges 17 of the two lips 8a, in the closed state of the pinching closing device 1.

Of course, to be able to implement the required interlocking, the two surfaces 13 and 14 are arranged head-to-foot relative to one another. If one is arranged in a U, the other is arranged in a ∩ (inverted U).

The surfaces 13 and 14 are mated in such a way as to be able to work together and to ensure the pinching of the tube T on itself until it is totally closed, whereby the cores 35 and 36 are mated together, just as, on the one hand, the wings 36a and 38a, and, on the other hand, the wings 36b and 38b. Like the indentations 11a, 11b, the pinching extends along the axis 6, i.e., it is not specific, but linear over a certain length.

The surfaces 13 and 14 are smooth overall. In the embodiment shown, the surfaces 13 and 14 have simple shapes and not distorted shapes.

In the embodiment shown, the cores 35 and 37 have an overall flattened shape with a slight curve, respectively concave and convex. The wings 36a, 36b, 38a, 38b have an overall flattened shape.

The two wings 36a and 36b of the pair of wings 36a, 36b of the female indentation 11a diverge slightly from the core 35 in such a way that the opening of the female indentation 11b is slightly tapered. These wings 36a and 36b are connected to the core 35 by two rounded parts 39 with a fairly large radius of curvature.

The two wings 38a and 38b of the pair of wings 38a, 38b of the male indentation 11b are slightly convergent from the second core 7b that constitutes the base of the projection 15. These wings 38a and 38b are connected to the core 37 by two rounded parts 40 with a fairly large radius of curvature.

The surfaces 13 and 14 have overall analogous contours, as it is described. They are intended to be arranged as a whole in the same direction. They are offset transversely from one another as a result of the presence between them of the tube T that is positively pinched and closed because of the geometry that they exhibit. They are thus held in place thanks to locking means, which will be referenced again.

The pinching closing device 1 and its constituent parts (cross-sections 3 and parts 4 and 5) can be found in one of the following two states: open state and closed state.

In the open state (FIGS. 1 and 3), the two cross-sections 3a and 3b are separated and dissociated from one another. The two cross-sections 3a and 3b can then be manipulated, each one separately. In this open state, the two cross-sections 3a and 3b allow a free access that is transversal to the indentations 11a and 11b, each of them not being covered by the cross-section to which the other indentation belongs.

In the open state, the tube T can, in any longitudinal region that is desired for being a pinching region RP, be introduced into—or if necessary removed from—the female indentation 11a that forms a cradle, without its shape being affected, in particular if it is pinched or flattened, with the circulation, the passage for cutting into sections, the communication of the fluid into the tube T not being blocked, prevented, or impeded. The cradle of the female indentation 11a is, of course, matched to the shape and to the transverse dimension of the tube T.

Thus, the open state makes possible the installation phase of the tube T in the pinching closing device 1, and optionally its removal (FIGS. 1 and 3).

In the closed state (FIG. 2), the two cross-sections 3a and 3b are close to one another and interlocked, with the two lips 8a of the first male cross-section 3a being housed with holding contact, in the two lips 8b of the second female cross-section 3b.

In the closed state, the two outside surfaces 9 of the first lips 8a are in contact and supported on the two inside surfaces 10 of the second lips 8b, and, if necessary—as indicated above—the two small surfaces 16 are in contact and supported on the two free edges 17 of the second lips 8b.

In the closed state, the pinching closing device 1 has a general outside shape that is essentially that of a parallelepiped with an at least essentially square transverse cross-section, elongated along the axis 6, and whose four edges 18 that extend axially are rounded. This parallelepiped comprises two free ends or transverse end surfaces and distal surfaces 19 (FIG. 5).

Reference is made to the case where the pinching closing device 1 is part of a pinching closing unit for cutting into sections 1+2, whereby each cross-section 3a, 3b comprises two parts 4a and 4b, 5a and 5b.

Each of the parts 4a, 4b, 5a, 5b is terminated from the exterior side by a free end or transverse distal end surface 19 and from the interior side by a transverse end surface and proximal surface, namely, respectively, 20a, 20b, 21a, 21b (FIGS. 5 and 6). These transverse end surfaces and proximal surfaces are essentially planar.

In the closed state, the two parts 4a and 4b, 5a and 5b of each of the two cross-sections 3a and 3b have their two transverse end surfaces and proximal surfaces 20a and 20b, 21a and 21b located opposite one another and in the immediate proximity of one another but nevertheless offset from one another, along the longitudinal axis 6, in such a way as to make a median transverse passage for cutting into sections 22. The two transverse end surfaces and proximal surfaces 20a and 21a of the parts 4a and 5a, like the two transverse end surfaces and proximal surfaces 20b and 21b of the parts 4b and 5b, are coplanar or essentially coplanar.

In the closed state, the two indentations 11a and 11b no longer have free transverse access as in the open state, but between them they make a positive pinching closing passage 23, with an axis 6, forming a type of hollow channel, limited by the two surfaces 13 and 14 of the indentations 11a and 11b, and the part of the small surfaces 16 that are adjacent to the projection 15.

In this embodiment of the pinching closing unit for cutting into sections 1+2, the positive pinching closing passage 23 is in two positive pinching closing segments 23a that are placed in the line of extension of one another. These two segments 23a first come out from the two transverse end surfaces and distal surfaces 19 to the outside of the pinching closing device 1. These two segments 23a next come out from the two pairs of transverse end surfaces and proximal surfaces 20a, 21a and 20b, 21b.

Between the two pairs of transverse end surfaces and proximal surfaces 20a, 21a and 20b, 21b, the positive pinching closing passage 23 is absent to the point where it does not exist, with the pairs of parts 4a, 5a and 4b, 5b being offset from one another in the axial direction, over a small distance, as indicated above.

The two positive pinching closing segments 23a are therefore placed in the extension of one another but with a small separation between them 23b.

By referring to FIG. 4, "positive pinching closing zone" ZPF of the tube T is conventionally called the longitudinal segment of the tube T that is to the right of the parts 4a and 5a, 4b and 5b of the pinching closing device 1, in the two positive pinching closing segments 23a of passage 23. "Flattening zone" ZA of the tube T is called the longitudinal segment of the tube T that is between the parts 4a and 5a, 4b and 5b of the pinching closing device 1, in the separation 23b between the two segments 23a of the passage 23. The pinching region RP of the tube T, already mentioned, consists of the longitudinal segment of the tube T that comprises the two positive pinching closing zones ZPF and the flattening zone ZA that is placed between them.

In this embodiment, the parts 4a and 4b, on the one hand, and 5a and 5b, on the other hand, are analogous, in such a way that the pinching closing device 1 ensures a closing function of the tube T on itself in the two positive pinching closing zones ZPF, extending over a certain axial length, separated from one another by the flattening zone ZA. In this zone, the tube T is held in place without a total closing being positively ensured. This holding of the tube T in place facilitates its cutting into sections, with the pinching closing device 1 forming a part here of a pinching closing unit for cutting into sections 1+2.

In another embodiment of such a unit, it is possible to provide that the pinching closing device 1 ensures a closing function of the tube T on itself in a single positive pinching closing zone ZPF. In the preceding embodiment, this which was the other positive pinching closing zone ZPF can only ensure the positive holding in place, without total closing, with the flattening zone ZA then playing the same role as in the preceding embodiment. In this case, it is essential that the hollow parts ensuring this simple positive holding in place comprise indentations such as those described above.

The pinching passage 23, in the transverse straight cross-section, has a U shape, as a result of the corresponding shape of the indentations 11a, 11b. This passage 23 consequently comprises a core 41 and two wings 42a and 42b, respectively corresponding to the cores 35 and 37 and to the wings 36a, 38a and 36b, 38b.

The tube T that is arranged in the pinching passage 23 of the pinching closing device 1 in the closed state, restricted by the contoured passage 23, is formed by being, on the one hand, flattened on itself and thus closed, and, on the other hand, shaped in a U, with a core Ta and two wings Tb, terminated by two end folds Tp.

The width (in a transverse plane) of the opening that forms the pinching passage 23—core 41 and wings 42a and 42b—is defined by the transverse separation between the inside surface 13 and the surface 14, namely the transverse separation between the cores 35 and 37, on the one hand, and the wings opposite the pairs of wings 36a and 38a, 36b and 38b.

In the closed state, the two wings 36a and 38a, 36b and 38b of each pair of wings opposite the male indentation 11a and the female indentation 11b will draw together toward their ends 43 that are opposite the cores 35 and 37 of the indentations, at least in the zone of these ends 43. The cross-sections 3a and 3b are arranged accordingly.

In the embodiment shown, the two wings 36a and 38a, 36b and 38b will draw together in a more or less continuous way from the cores 35 and 37 to the opposite ends 43.

As a result, each of the two wings 42a and 42b of the passage 23 has—between the surfaces 36a, 38a and 36b, 38b of the two indentations—an opening whose width will diminish toward its end that is opposite to the core 41 of the passage 23, and in particular will diminish more or less continuously from the core 41.

The greatest width of the passage 23 is slightly smaller than twice the thickness of the wall of the tube T, based on the compressibility of the tube T, in such a way that the tube T—once placed in the pinching closing device 1 in the closed state—is compressed on itself, and the device ensures a closing function of the tube T on itself.

As a consequence of the fact that the width of the passage 23 will diminish, toward its end opposite the core 41, the tube T is more heavily compressed in the zone of its two folds Tp. This arrangement makes it possible to prevent a small opening of the tube on itself from persisting in the zone of folds since such an opening has the effect of allowing one or more drops of fluid of the tube T to flow from it during the pinching closing and the cutting of the tube T into sections.

Thus, the pinching closing device 1 performs a function of closing the tube T on itself in the pinching region, preventing any passage of the fluid into the tube T.

Once the tube T, in the installation phase, positioned in the female indentation 11a, whereas the pinching closing device 1 is in the open state, the pinching closing device 1 is brought into the closed state; the tube T is clasped in the passage 23 in the pinching phase.

In the pinching phase, the tube T is positively pinched and closed in its two positive pinching closing zones ZPF by the surfaces 13 and 14 and the cooperation of the indentations 11a and 11b. Between the two positive pinching closing zones ZPF, the tube T is not positively pinched and closed, but it is flattened more or less significantly to a certain degree, which justifies that this segment of the tube T is referred to as flattening zone ZA. As a result of the positive pinching closing, the tube T is closed on itself in the pinching region RP, which prevents the circulation, the passage, and the communication of fluid on either side of this region.

With at least one cutting element 2, the tube T can also, in a phase for cutting into sections that follows the pinching phase, be cut into sections transversely in the passage for cutting into sections 22, in the flattening zone ZA, and therefore in the pinching region RP. With the cutting into sections taking place after the closing, it is in no way disturbed by the fluid that is found in the tube T. With the closing being total, the risk that one or more drops of fluid will flow from the tube T is avoided.

The shapes and dimensions of the pinching closing device 1 are adapted to the nature, the shape and the dimensions of the tube T, in such a way that the desired pinching closing relative to the tube T is correctly achieved.

In the embodiment of FIG. 3, the female indentation 11a and the male indentation 11b have the same shape, the same arrangement and the same dimensions, constant and uniform, from one free and distal end 19 to the other free and distal end 19, via the proximal ends.

So as to be able to be placed and held in place in the extension of one another (FIG. 3), the two parts 4a and 4b or 5a and 5b of the same cross-section 3a or 3b are structurally and functionally combined with one another, in a removable way, by combination means.

More specially, the two parts 4a and 4b or 5a and 5b are combined by their end surfaces and proximal surfaces, respectively 20a and 20b, on the one hand, and 21a and 21b, on the other hand (offset along the axis 6 for forming the passage for cutting into sections 22), thanks to combination means 24a and 24b that belong to the parts 4a and 4b, on the one hand, and 5a and 5b, on the other hand.

In the embodiment of FIGS. 3 and 6, the combination means 24 comprise several (here, four, but the number can be different) projections or lugs that form studs 24a that are made on the end surfaces and proximal surfaces 20a, 20b, 21a, 21b of one of the two parts 4a, 4b, 5a, 5b, able to cooperate in a removable way with a number that is equal to blind holes or hollows forming cavities 24b—complementary and made on the end surfaces and proximal surfaces 20b, 20a, 21b, 21a of the other of the two parts 4b, 4a, 5b, 5a.

These projections 24a and these holes 24b extend parallel to the axis 6 and therefore to the direction of extension of the tube T when it is positioned in the pinching closing device 1. Their cooperation is achieved by an axial sliding parallel to the axis 6. Their dimensions are such that the projections 24a are housed with minimal play in the holes 24b.

So that the holding in place of parts 4a and 4b, on the one hand, and 5a and 5b, on the other hand, is ensured in an effective way, the projections 24a and the holes 24b are arranged in pairs of lips 8a, on the one hand, and 8b, on the other hand, on either side of the indentations 11a and 11b and of the passage for cutting into sections 22.

So as not to obstruct the access and the opening of the passage for cutting into sections 22, it is provided that no projection and no hole such as 24a, 24b is to the right of cores 7a and 7b.

According to other embodiments, the number of projections 24a and holes 24b is different, or—on the same given end surfaces and proximal surfaces 20a, 20b, 21a, 21b—not one or more projections 24a or holes 24b, but rather a combination of projections 24a and holes 24b is provided.

The transverse passage for cutting into sections 22 is produced by the presence of separation means that are provided to this end. These separation means consist of stops made either on the end surfaces and proximal surfaces 20a, 20b, 21a, 21b or on the combination means 24a, 24b; for example, the projections 24a are locked at the end of travel in the holes 24b.

In the embodiment of the pinching closing device 1 that is shown in FIG. 1, the two cross-sections 3a and 3b comprise reciprocal-locking means 25a and 25b of the two cross-sections 3a and 3b and parts 4a and 5a in the closed state. These locking means 25a and 25b are irreversible, with the two cross-sections 3a and 3b once brought to the closed state being held in place in this state by the locking means 25a and 25b, without being able to be dissociated.

Thus, once the tube T that is housed in the passage 23 has been pinched and closed, with the pinching closing device 1 having been brought to the closed state, the tube T is thus held in place pinched and closed, and it remains in this state, with the pinching closing device 1 being combined with the tube T as a result of the irreversibility of the locking means 25a and 25b.

In the embodiment of the pinching closing unit for cutting into sections 1+2 that is shown in FIG. 3, in which the positive pinching closing takes place in two positive pinching closing zones ZPF, the two cross-sections 3a and 3b comprise reciprocal-locking means 25a and 25b of the two cross-sections 3a and 3b and two pairs of parts 4a, 5a and 4b, 5b in the closed state.

In one variant of this embodiment, the irreversibility of the locking means 25a and 25b is provided for only one of the two pairs of parts 4a, 5a and 4b, 5b. This variant is useful when it is desired that one end for cutting into sections is closed without the necessity that the other end for cutting into sections also be closed, with the corresponding parts of the cross-sections 3a and 3b then being able to be removed.

In another embodiment of a pinching closing unit for cutting into sections 1+2 where the pinching closing device 1 ensures a closing function of the tube T on itself in a single positive pinching closing zone ZPF, with the other zone ensuring only a holding in place without total closing, it is also possible to provide that the irreversibility of the locking means 25a and 25b is provided only for the parts of cross-sections 3a and 3b that ensure the positive pinching closing, but it is not provided for the parts that ensure only a holding in place without total closing.

In the embodiment of FIGS. 3 and 6, the reciprocal-locking means 25a and 25b are two units that comprise a series of contoured, irreversible hooking teeth (or catches), oriented in two opposite directions, extending axially, made respectively on the two outside surfaces 9 of the first lips 8a and the two inside surfaces 10 of the second lips 8b in their interlocking zone.

Instead of teeth, it is possible to provide catches or the like.

In the embodiment of FIGS. 1 to 3, the reciprocal-locking means 25a and 25b are brought to cooperate with one another sequentially to a sliding movement for drawing together the two cross-sections 3a and 3b in a transverse direction, leading to the interlocking with force of the two cross-sections 3a and 3b, with the teeth 25a and 25b becoming engaged mutually in an irreversible way.

The passage for cutting into sections 22 empties onto the outside surface of the pinching closing device 1 by at least one access, in this case an access slot 26 that can allow the introduction into the passage for cutting into sections 22—and the removal from the passage for cutting into sections 22—of the cutting element 2, by a transverse sliding movement or an element for control of the movement of the cutting element 2. On the other hand, the pinching passage 23 empties into the passage for cutting into sections 22.

In the embodiment of FIGS. 3 and 6, the passage for cutting into sections 22 goes through the slot 26 to an analogous diametrically opposed slot that is also located on the periphery of the pinching closing device 1. In another embodiment, not shown, the passage for cutting into sections 22 does not go through or is blind, not emptying into the diametrically opposed periphery of the pinching closing device 1, in which case there is only a single slot 26.

When two diametrically opposed slots are provided, it is possible, according to the embodiments, to provide a single cutting element 2 (or element for control of the movement of the cutting element 2) or two opposite cutting elements 2 (or control elements), each being introduced by a dedicated slot.

The passage for cutting into sections 22 also empties into—and interferes with—the space or separation 23a that is located between the two positive pinching closing segments 23a.

The access 26, arranged transversely, like the passage for cutting into sections 22, comprises a large side or length and a small side or width. The large side extends transversely to the right of the opening of the cradle of the surface 13 of the first indentation 11a, and it has a length that is at least slightly larger than this opening. With this constructive arrangement, it is ensured that the cutting element 2 will duly interfere with the entire transverse cross-section of the tube T that is held in place pinched and closed in the two positive pinching closing segments 23a and that goes through the space or separation 23b that is located between them. And thus the cutting element 2 can transversely cut into sections the tube T in the space or separation 23b.

For this purpose, the combination means 24a, 24b of the cross-sections 3 are spaced from the surface 13 in such a way as to allow the passage of the cutting element 2 between the combination means 24a, 24b, without cutting them or even hardly touching them.

The small side of the access 26 is arranged axially. Its small length is matched to the thickness of the cutting element 2 (or the element for control of the movement of the cutting element 2) in such a way as to allow the passage and the guiding of the cutting element 2 (or the control element) in the passage for cutting into sections 22, without the cutting element 2 cutting or even hardly touching the pinching closing device 1 itself.

The passage for cutting into sections 22 and the access 26 are sized based on the dimensions of the pinching closing device 1, the nature of the shape and dimensions of the tube T, as well as dimensions of the cutting element 2 or the control element of the element of the cutting element 2, in such a way as to ensure an effective cutting into sections.

Of course, the degrees of play necessary for the movement of the cutting element are provided.

The pinching closing device 1 that was just described is implemented as it is now described for the purpose of pinching and closing a tube T and, if necessary and then in combination with the at least one cutting element 2, within the framework of a pinching closing unit for cutting into sections 1+2—for the purpose of transversely cutting the tube T.

There is a pinching closing device 1 that is in, or is brought into, the open state and of which each cross-section 3a and 3b comprises its two parts 4a and 4b, and 5a and 5b that are combined thanks to combination means 24a and 24b.

There is the tube T that, in this situation, is continuous and normally shaped for allowing fluid to pass.

The tube T is positioned in the desired pinching region RP of the latter, in the female indentation 11a of the first male cross-section 3a (installation phase). For example, the first male cross-section 3a is arranged so that its surface 13 is rotated frontally toward the operator or is rotated to be within the view of the operator. In the embodiment of FIG. 1, the first male cross-section 3a is arranged approximately with the horizontal axis 6, its surface 13 rotated upward.

The second female cross-section 3b is brought opposite the first male cross-section 3a, whereby the surfaces 13 and 14 are rotated toward one another. In the embodiment of FIG. 3, the second female cross-section 3b is arranged above the first male cross-section 3a, approximately with the horizontal axis 6, its surface 14 rotated downward perpendicular to the surface 13.

By a relative movement of drawing together the first and second cross-sections 3a and 3b, and parts 4a and 4b, on the one hand, and 5a and 5b, on the other hand, in this case by a relative movement of transverse sliding, the pinching closing device 1 is passed through (its cross-sections 3 and parts 4 and 5) from the prior open state to the subsequent closed state. In the embodiment of FIG. 3, this relative movement of transverse sliding is a vertical movement.

This closing movement is continued until the end of travel, whereas the tube T is positively pinched until being closed in its two positive pinching closing zones ZPF by the surfaces 13 and 14 that deform it and thus restrict it, given the geometric relation that exists between the tube T and the two positive pinching closing segments 23a of the passage 23 (pinching phase).

This closing movement is facilitated as a result of the irreversible locking means 25a, 25b, i.e., nonreturn means.

By bringing the pinching closing device 1 into the closed state, the reciprocal-locking means 25a and 25b are made to cooperate simultaneously to keep closed the two parts 4a and 5a, on the one hand, and 4b and 5b, on the other hand, of each pair of parts of the first and second cross-sections 3a and 3b, in the position where the tube T is pinched and closed.

The tube T is thus kept pinched and closed between the two cross-sections 3a and 3b of the pinching closing device 1.

In one embodiment, it may be enough to leave it as is, with the pinching closing device 1 remaining attached to the tube T. In this case, the tube T remains integral and is not cut into sections.

In another embodiment, it is also desired to cut the tube T into sections in the pinching region RP so as to obtain a tube T that is cut into sections in two lengths, each of them pinched and closed at its end part that is cut into sections or, as indicated above, only one is pinched and closed, and the other is only held in place.

In this case, there is also at least one cutting element 2.

Whereas the pinching closing device 1 is in the closed state around the tube T, in a phase for cutting into sections, the tube T is cut after its pinching and its closing have been carried out in the flattening zone ZA, in which the tube is not positively pinched but nevertheless flattened. According to the embodiments, the tube T is cut into sections immediately after or a certain time after its positive pinching closing has been implemented.

For this purpose, the cutting element 2 is brought opposite to the access 26 of the pinching closing device 1.

Then, by a relative movement of drawing together the cutting element 2 and the pinching closing device 1, in this case a transverse sliding movement of the cutting element 2 in its own plane, the cutting element 2 is introduced via its end into the access 26, and the movement is continued until the cutting element 2 further penetrates into the passage for cutting into sections 22, and then into the space or separation 23b where it interferes with the tube T in its flattening zone ZA between the pairs of proximal surfaces 20a, 21a and 20b, 21b. It is thus that the tube T is cut or cut into sections transversely.

In this movement, the cutting element 2 is, if necessary, guided by the pairs of proximal surfaces 20a, 21a and 20b, 21b, and also, if necessary, by the combination elements 24a, 24b.

Thus, the tube T is cut into sections without the cutting element 2 cutting into sections, penetrating into or interfering frontally with the pinching closing device 1. As a result, the appearance of troublesome chips or waste originating from the pinching closing device 1 is avoided.

According to the embodiments, the sliding movement of the cutting element 2 is continued on either side of the pinching closing device 1 if the passage for cutting into sections 22 goes through or is stopped in a suitable position if the passage for cutting into sections 22 does not go through and is blind. According to the embodiments, the cut is made by means of a single cutting element 2 or two opposite cutting elements 2.

According to the embodiments, the cutting element 2 is passed into the passage for cutting into sections 22 without contact with the pinching closing device 1 (FIG. 4) or on the contrary with a surface contact that slides with the pinching closing device 1 (FIG. 9).

Once the tube T is cut into sections in its flattening zone ZA, the cutting element 2 can be removed either because it passed through on either side of the pinching closing device 1 if the passage for cutting into sections 22 goes through, or by a sliding movement in the direction opposite to the direction of introduction if the passage for cutting into sections 22 does not go through and is blind.

In this situation, it is then possible to dissociate the parts 4a and 4b, on the one hand, and the parts 5a and 5b, on the other hand, by dissociating from one another the combination means 24a and 24b by an axial sliding movement of separation (dissociation phase). However, the parts 4a and 5a, on the one hand, and 4b and 5b, on the other hand, are left attached to the end parts of the tube T that are cut into sections by pinching them and by closing them.

Then, a tube T is obtained that is cut into sections of two segments or lengths, each pinched and closed at its end part that is cut into sections, to which is attached for this purpose one pair of parts, respectively 4a and 5a, on the one hand, and 4b and 5b, on the other hand.

Or, as indicated, a tube T is obtained that is cut into sections of two segments or lengths, which is pinched and closed on one side.

According to a variant embodiment, the pinching passage 23 has an adjustable opening for adapting to tubes T of different geometries, in particular sizes.

For this purpose, it can be provided in one embodiment to use different devices 1 that correspond to different geometries, in particular sizes, which makes it possible to cover a wide spectrum of geometries of tubes T.

In another embodiment (FIG. 2), it is provided that the relative movement of drawing together and closing the first and second cross-sections 3a and 3b is more or less large, in such a way that the pinching passage 23 is respectively more or less small. This is made possible as a result of the existence of reciprocal-locking means 25a and 25b, comprising a series of stepped contoured hooking teeth between the core 7a, 7b of the cross-section 3a, 3b and the free border of the edge of the adjacent lip 8a, 8b; this makes possible different relative positions for locking cross-sections 3a and 3b by a nonreturn.

In one embodiment (FIG. 5), it is provided that one and/or the other of the two indentations 11a and 11b is slightly inclined along the axis 6, toward the free border of the edge of the lip 8a, 8b and toward the proximal end 20a, 20b, 21a, 21b.

This constructive arrangement makes it possible to exert a more significant pinching of the tube T toward this proximal end 20a, 20b, 21a, 21b, which is such that it expels the fluid found in the tube T toward the other distal end 19.

According to one embodiment (FIG. 7), the combination means 24a and 24b comprise a projection 24a and a groove 24b, made on the end surfaces and proximal surfaces 20a, 20b, 21a, 21b, and extend in a non-parallel manner to the axis 6 as in the embodiment of FIGS. 3 and 6, but extend transversely. In this case, the combination or dissociation movement is a transverse sliding movement parallel to the direction of the projection 24a and the groove 24b and not an axial movement.

According to another embodiment (FIG. 8), the combination means 27 differ from the projection combination means 24a and hole or groove 24b, as described above, and comprise a removable connecting part in the form of a clip 27, able to combine in a removable way the two parts 4a and 4b or 5a and 5b in a way that is not direct but indirect.

This clip 27 comprises a flat core 28, able to come, when the clip is mounted in a combination situation, against the outside surface of the pinching closing device 1. This core 28 is pierced by a slot 26a that can come perpendicular to the access 26 and can superpose itself on it.

From the core 28, four (or more) projections that are in rod form 29a, contoured, parallel to one another and orthogonal to the core 28 are adjacent. These projections 29a are able to work with an equal number of transverse grooves 29b that are made on the outside surface of the pinching closing device 1 on each part 4a, 4b, 5a and 5b.

In the different embodiments described above, the two parts 4a and 5a, on the one hand, and 4b and 5b, on the other hand, of the two cross-sections 3a and 3b are separate parts and the relative closing movement is a transverse sliding movement in translation.

In another embodiment (FIGS. 11 and 12), the two parts 4a and 5a, on the one hand, and 4b and 5b, on the other hand, of the two cross-sections 3a and 3b are parts that are not separate but combined structurally with one another to pivot around a pivoting axis 30 that is parallel to the axis 6, and the relative closing movement is not a transverse sliding movement in translation but a pivoting movement around the pivoting axis 30. The pivoting axis 30 is offset very broadly relative to the axis 6, on a longitudinal side of the pinching closing device 1, in such a way that—the pivoting radius being large—the end of the interlocking pivoting movement differs little from a transverse sliding, as above.

From the longitudinal side opposite the axis 6, there are provided locking means 25a and 25b, one of which comprises a female part 31a, connected to one of the parts 4a, 5a or 4b, 5b, and equipped with teeth 25a, and the other of which comprises a male part 31b, connected to the other part 5a, 4a or 5b, 4b, and equipped with teeth 25b.

The teeth 25a, 25b, as above, are contoured irreversible hooking teeth, oriented in two opposite directions, extending axially.

In the embodiment of FIGS. 11 and 12, as in the embodiment of FIG. 8, the combination means 32 comprise, in line with the part 27, a removable connecting part in the shape of a cradle 32, able to combine in a removable way the two parts 4a and 4b or 5a and 5b in a way that is not direct but indirect.

This part 32 comprises a cradle 33, able to come, when the part 32 is mounted in a combination situation, against the outside surface of the pinching closing device 1, on one side of the latter, in such a way as to leave the other side free, or the passage for cutting into sections 22 is accessible.

The cradle 33 comprises two lips 34 that face one another, able to encircle the parts 4a and 4b or 5a and 5b by their distal end surfaces 19.

In the embodiments described above of a pinching closing unit for cutting into sections 1+2, the pinching closing device 1 structurally does not include the at least one cutting element 2, with the latter, however, being combined functionally.

According to other embodiments, the pinching closing device 1 structurally and functionally includes at least one cutting element 2. For example, in the case of FIG. 9, the cutting element 2 forms a sort of guillotine that has a general elevated U shape and is mounted to slide in its own plane over the proximal end surface 20a or 20b of one of the parts 4a, 4b that is equipped with suitable guiding means. In this embodiment, there is provided a single cutting element 2 or two cutting elements on the two end surfaces 20a and 20b. In this embodiment, the access 26 allows the passage of an element for control of the movement of the cutting element 2, such as a type of blade.

The invention claimed is:

1. A pinching closing device (1) for pinching a flexible tube in a pinching region, comprising:
   two cross-sections (3a, 3b), each cross-section having a hollow part (4a, 5a) with a male indentation (11b) and a female indentation (11a), respectively, able to be either in the open state where they are separated from one another or in the closed state where they are drawn together and closed on one another by reciprocal-locking means (25a and 25b) and where surfaces (13 and 14) of the indentations (11a and 11b) form a positive pinching passage (23) of the tube, wherein,
   in the transverse straight cross-section, the male indentation (11b) has a U shape with a core (37) and two wings (38a and 38b); in the transverse straight cross-section, the female indentation (11a) has a U shape with a core (35) and two wings (36a and 36b); and in the transverse straight cross-section, the pinching passage (23) has a U shape with a core (41) and two wings (42a and 42b),
   the two wings (36a, 38a and 36b, 38b) opposite each pair of wings facing the male indentation (11a) and the female indentation (11b) will draw together toward their ends (43) that are opposite to the cores of the indentations (35 and 37), at least in the zone of these ends (43), and each of the two wings (42a and 42b) of the pinching passage (23) has, between the surfaces of the two indentations (11a and 11b), an opening whose width will diminish towards its end that is opposite to the core (41) of the pinching passage (23),
   the width of the opening of the pinching passage (23) is at most slightly smaller than twice the thickness of the wall of the flexible tube to be pinched, and
   the pinching device (1) is disposable and performs an operation of the tube closing on itself in the pinching region preventing any passage of fluid into the tube.

2. Pinching closing device (1) according to claim 1, wherein the locking means (25a and 25b) are irreversible, with the two cross-sections (3a and 3b)—once brought into the closed state—being held in place in this state by locking means (25a and 25b) without being able to be dissociated, and comprise contoured hooking teeth, oriented in two opposite directions.

3. Pinching closing device (1) according to claim 2, wherein the pinching passage (23) has an adjustable opening, with the relative movement for bringing one cross-section (3b) opposite the other (3a) and the pinching closing device (1) in the closed state being more or less large, so that the pinching passage (23) is respectively more or less small.

4. Pinching closing device (1) according to claim 3, wherein it comprises a series of stepped hooking teeth (25a and 25b), making possible different relative locking positions of the cross-sections (3a and 3b) so that the pinching passage (23) is more or less small.

5. Pinching closing device (1) according to claim 1, wherein the two cross-sections (3a and 3b) are two separate parts and are brought to the closed state by a relative transverse sliding movement, whereby one (3a) of the two cross-sections (3a and 3b) is a male cross-section and the other (3b) is a female cross-section, whereby the male cross-section (3a) comprises and is limited on the outside by a first core (7a) and two first lips (8a), with the female cross-section (3b) comprising and being limited on the outside by a second core (7a) and two second lips (8b).

6. Pinching closing device (1) according to claim 5, wherein the separation between the two opposite outside surfaces (9) of the two first lips (8a) corresponds to the separation between the two inside surfaces (10) opposite the two second lips (8b), in such a way as to allow, in the closed state of the pinching closing device (1), the interlocking with adjustment of the two cross-sections (3a and 3b), with the pair of outside surfaces (9) then being in contact and supported on the pair of inside surfaces (10), and wherein the reciprocal-locking means (25a and 25b) are two units that comprise a series of teeth respectively made on the two outside surfaces (9) of the first lips (8a) and the two inside surfaces (10) of the second lips (8b) in their interlocking zone.

7. Pinching closing device (1) according to claim 1, wherein the two cross-sections (3a and 3b) are two parts that are structurally combined with one another to pivot around an axis (30) that, relative to the longitudinal axis of the pinching closing device (1), is offset on a longitudinal side of the pinching closing device (1), with the two cross-sections (3a and 3b) being brought into the closed state by a relative pivoting movement around the pivoting axis (30).

8. Pinching closing device (1) according to claim 7, wherein the reciprocal-locking means (25a and 25b) comprise teeth that are located on the side opposite to the axis and in particular comprise a female part (31a) that is connected to one of the parts (4a) and equipped with teeth (25a) and a male part (31b) that is connected to the other part (5a) and equipped with teeth (25b).

9. Pinching closing device (1) according to claim 1, wherein the two cross-sections (3a and 3b) have the same axial length.

10. Pinching closing device (1) according to claim 1, wherein the two indentations (11a and 11b) have the same shape, the same arrangement, and the same dimensions, constant and uniform, from one free end to the next, or one and/or the other of the two indentations (11a, 11b) is slightly inclined along the axis (6) of the pinching closing device (1), toward the free border of the edge of the lip (8a, 8b) and toward the proximal end, for exerting a more significant pinching of the tube toward the proximal end and for expelling the fluid that is in the tube toward the distal end (19).

11. Pinching closing device (1) according to claim 1, wherein the cross-sections (3a and 3b) are contoured and extend along the longitudinal axis (6), with the positive pinching closing zone (ZPF) extending over a certain axial length.

12. Pinching closing device (1) according to claim 1, wherein each cross-section (3a and 3b) comprises two hollow parts (4a, 4b and 5a, 5b) that are placed in the extension of one another by combination means (24a, 24b, 27, 32), with at least one pair (4a and 5a) of parts having indentations (11a, 11b).

13. Pinching closing device (1) according to claim 12, wherein the two hollow parts (4a, 4b and 5a, 5b) of each cross-section (3a and 3b) are either analogous, with the pinching closing device (1) ensuring a closing function of the tube on itself in two positive pinching closing zones, or different, with the pinching closing device (1) ensuring a closing function of the tube on itself in a single positive pinching closing zone and being only held in place in the other zone.

14. Pinching closing device (1) according to claim 12, wherein the locking means (25a and 25b) are either irreversible for the two pairs of hollow parts (4a and 5a, 4b and 5b), or irreversible for one of the pairs of hollow parts (4a and 5a or 4b and 5b) and reversible for the other (4b and 5b or 4a and 5a).

15. Pinching closing device (1) according to claim 12, wherein the combination means (24a, 24b, 27, 32) comprise at least one projection (24a) made on one of the parts (4a, 4b, 5a5b), able to work in a removable way with at least one blind hole or hollow or groove (24b)—complementary and made on the other part of the same cross-section (3a, 3b).

16. Pinching closing device (1) according to claim 12, wherein the combination means (27) comprise at least one removable connecting part in the form of a clip (27), able to combine the two parts (4a and 4b or 5a and 5b) in a removable way and in an indirect way, with the clip (27) comprising a core (28) from which four projections that are in rod form (29a) and that are able to work with four transverse grooves (29b) made on the outer surface of the pinching closing device (1) are adjacent, on each part (4a, 4b, 5a, 5b).

17. Pinching closing device (1) according to claim 12, wherein the combination means (32) comprise a removable connecting part in the shape of a cradle (32), able to combine the two parts (4a and 4b or 5a and 5b) in a removable way and in an indirect way, with the cradle (33) comprising two lips (34) that face one another, able to encircle the parts (4a and 4b or 5a and 5b) by their distal end surfaces (19).

18. Pinching closing device (1) according to claim 12, wherein the hollow parts (4a, 4b and 5a, 5b) are placed in the extension of one another by making between them a median passage (22) that empties onto the outside surface of the device by an access (26), whereby the positive pinching closing passage (23) comprises at least one segment (23a) to which a space (23b)—into which the passage (22) empties and where the tube is held in place, on the one hand, and flattened to a certain degree, on the other hand—is axially adjacent, and
wherein the functions of the access (26), on the one hand, and the median passage (22), and the space (23b), on the other hand, are respectively to allow, on the one hand, the introduction, and, on the other hand, the passage of an element (2) for cutting the tube in its zone located in said space (23b).

19. A pinching closing device (1) for pinching a flexible tube in a pinching region, comprising:
a first part (4a) extending in an axial direction, the first part (4a) comprised of a first core (7a) extending in the axial direction and two first lips (8a), extending in a first direction, off opposite edges of the first core (7a), the first part (4a) having a first cross-sections (3a) with a female indentation (11a) defining a first surface (13), the two first lips (8a) having outside surfaces (9) facing away from each other, each of the two first lips (8a) having a free end edge (17); and a second part (4b) extending in the axial direction, the second part (4b) comprised of a second core (7b), two second lips (8b) extending, in a second direction opposite the first direction, off of opposite edges of the second core (8b), and a projection (15) extending from two spaced-apart inside surfaces (16) of the second core (7b), at a location intermediate the two opposite edges of the second core (8b) and in the second direction, off the second core (7b), the second part (4b) having a second cross-section (3b) with a male indentation (11b) defining a second surface (14), the two second lips (8b) having an inside surfaces (10) facing toward each other, the first and second parts (4a, 4b) further comprising reciprocal-locking means (25a and 25b), the reciprocal-locking means (25a and 25b) comprising two series of contoured, irreversible hooking teeth, the hooking teeth of the first series of teeth oriented in an opposite direction to the hooking teeth of the second series of teeth, the two series of teeth extending in the axial direction, the first series of teeth located on the outside surface (9) of each of the first lips (8a), and the second series of teeth located on the inside surface (10) of each of the second lips (8b), the first and second parts being in i) an open state when separated from one another, and ii) a closed state when drawn together and closed on one another by the reciprocal-locking means (25a and 25b) with the free end edges (17) of the two first lips (8a) contacting the two inside surfaces (16) of the second core (7b), wherein, the tube has a wall with a first wall thickness, in the closed state with the tube inserted between the first and second surfaces (13, 14), the first and second surfaces (13, 14) together form a positive pinching passage (23) with a passage core (41) and two passage wings (42a, 42b) extending from opposite edges of the passage core (41) in the first direction, a width of each passage wing (42a, 42b) continuously diminishing in the first direction from a maximum width at the passage core (41) to a minimum width at an upper end of each passage wing adjacent the inside surfaces (16) of the second core (7b), with the first surface (13) shaping a lower first wall section of the tube into a first U shape section and the second surface (14) shaping an upper second wall section of the tube into a second U shape section against the first U shape section, the first and second U shape sections together filing the passage core (41) and partially filling each of the two passage wings (42a, 42b), the partial filling of the two passage wings (42a, 42b) defining an open region at a top of each of the two passage wings (42a, 42b) between the first and second surfaces (13, 14) adjacent the inside surfaces (16) of the second core (7b), a top portion of each of the two passage wings, corresponding to a topmost part of the first and second U shape sections containing the first wall second against the second wall section, has a width that is at most slightly smaller than twice the first thickness of the wall of the tube to be pinched, and in the closed state, the tube is closed in the pinching region preventing any passage of fluid into the tube.

* * * * *